United States Patent
Becke et al.

(10) Patent No.: US 9,486,517 B2
(45) Date of Patent: Nov. 8, 2016

(54) VIRAL PARTICLE RELEASED AFTER INFECTION OF MAMMALIAN CELLS BY HUMAN CYTOMEGALOVIRUS (HCMV) CONTAINING A FUSION PROTEIN AND USE THEREOF

(75) Inventors: Sabine Becke, Mainz-Kastel (DE); Sabine Reyda, Rossdorf (DE); Bodo Plachter, Worrstadt (DE)

(73) Assignee: Vakzine Projekt Management GmbH (DE)

( * ) Notice: Subject to any disclaimer, the term of this patent is extended or adjusted under 35 U.S.C. 154(b) by 459 days.

(21) Appl. No.: 13/639,636

(22) PCT Filed: Apr. 6, 2011

(86) PCT No.: PCT/EP2011/001712
§ 371 (c)(1),
(2), (4) Date: Apr. 11, 2013

(87) PCT Pub. No.: WO2011/124371
PCT Pub. Date: Oct. 13, 2011

(65) Prior Publication Data
US 2013/0202708 A1    Aug. 8, 2013

(30) Foreign Application Priority Data
Apr. 6, 2010  (EP) .................................. 10003712

(51) Int. Cl.
*A61K 39/245*  (2006.01)
*C12N 7/00*  (2006.01)
*C12N 15/86*  (2006.01)

(52) U.S. Cl.
CPC ............... *A61K 39/245* (2013.01); *C12N 7/00* (2013.01); *C12N 15/86* (2013.01); *C07K 2319/40* (2013.01); *C12N 2710/16143* (2013.01); *C12N 2710/16162* (2013.01)

(58) Field of Classification Search
None
See application file for complete search history.

(56) References Cited

U.S. PATENT DOCUMENTS
2004/0152182 A1  8/2004  Plachter

FOREIGN PATENT DOCUMENTS
WO  WO2006/004661  1/2006

OTHER PUBLICATIONS

Mersseman Veronique et al: "Exogenous introduction of an immunodominant peptide from the non-structural IE1 protein of human cytomegalovirus into the MHC class I presentation pathway by recombinant dense bodies", Journal of General Virology, Society for General Microbiology, Spencers Wood, GB, vol. 89, No. Part 2, Feb. 1, 2008, pp. 369-379, XP002494811, ISSN: 0022-1317, DOI: DOI:10.1099/VIR.0.83380-0 cited in the application, the whole document.

Veronique Messeman et al: "Refinement of strategies for the development of a human cytomegalovirus dense body vaccine", Medical Microbiology and Immunology, Springer, Berlin, DE, vol. 197, No. 2, Mar. 5, 2008, pp. 97-107, XP019630565, ISSN: 1432-1831, cited in the application, the whole document.

Reap et al: "Development and preclinical evaluation of an alphavirus replicon particle vaccine for cytomegalovirus", Vaccine, Elsevier Ltd, GB, vol. 25, No. 42, Sep. 28, 2007, pp. 7441-7449, XP022277623, ISSN: 0264-410X, DOI: DOI:10.1016/J.Vaccine. 2007.08.016, the whole document.

Pepperl Sandra et al: "Dense bodies of human cytomegalovirus induce both humoral and cellular immune responses in the absence of viral gene expression", Journal of Virology, The American Society for Microbiology, US, vol. 74, No. 13, Jul. 1, 2000, pp. 6132-6146, XP002494810, ISSN: 0022-538X, DOI: DOI: 10.1128/ JVI.74.13.6132-6146, 2000, the whole document.

Becke S. et al: "Optimized recombinant dense bodies of human cytomegalovirus efficiently prime virus specific lymphocytes and neutralizing antibodies without the addition of adjuvant", Vaccine, Elsevier Ltd, GB, vol. 28, No. 38, Aug. 31, 2010, pp. 6191-6198, XP027211925, ISSN: 0264-410X [retrieved on Jul. 7, 2010], whole document.

Wills et al: "The Human Cytotoxic T-Lymphocyte (CTL) Response to Cytomegalovirus Is Dominated by Structural Protein pp65: Frequency, Specificity, and T-Cell Receptor Usage of pp65-Specific CTL", Journal of Virology 1996 (70,11), pp. 7569-7579.

Wills et al: "Adaptive Cellular Immunity to Human Cytomegalovirus", Caister Academic Press 2006, pp. 341-365.

Warming et al: "Simple and highly efficient BAC recombineering using galK selection", Nucleic Acids Res 2005 (33,4), pp. E36-12.

Walter et al: "Reconstitution of Cellular Immunity Against Cytomegalovirus in Recipients of Allogeneic Bone Marrow by Transfer of T-Cell Clones from the Donor", New England Journal of Medicine 1995 (333,16), pp. 1038-1044.

Utz et al: "Identification of a Neutralizing Epitope on Glycoprotein gp58 of Human Cytomegalovirus", Journal of Virology, 1989 (63), pp. 1995-2001.

(Continued)

*Primary Examiner* — Nicole Kinsey White
(74) *Attorney, Agent, or Firm* — Barnes & Thornburg LLP; Jeffrey R. Stone

(57) ABSTRACT

The present invention is related to a viral particle released after infection of mammalian cells by human cytomegalovirus (HCMV), wherein a) the particle is surrounded by a lipid membrane in which viral glycoproteins are embedded, b) the particle contains neither viral DNA nor capsids; and c) the particle contains a fusion protein comprising one or more parts of the T-cell antigen pp65 and at least one heterologous peptide, and wherein the at least one heterologous peptide is inserted at amino acid position W175 or A534 of the amino acid sequence of the T-cell antigen pp65.

20 Claims, 5 Drawing Sheets

(56) References Cited

OTHER PUBLICATIONS

Townsend et al: "Association of class I major histocompatibility heavy and light chains induced by viral peptides", Nature, vol. 340, Aug. 10, 1989, pp. 443-448.
Stratton et al: "Vaccines for the 21st Century: A Tool for Decisionmaking", The National Academies, 473 pages, (2000).
Schmolke et al: "Nuclear Targeting of the tegument Protein pp65 (UL83) of Human Cytomegalovirus: an Unusual Bipartite Nuclear Localization Signal Functions with Other Portions of the Protein to Mediate Its Efficient Nuclear Transport", Journal of Virology 1995 (69,2), pp. 1071-1078.
Schleiss et al: "Cytomegalovirus Vaccine Development", Curr Top Microbiol Immunol 2008 (325), pp. 361-382.
Robert H. Rubin: "The pathogenesis and clinical management of cytomegalovirus infection in the organ transplant recipient: the end of the 'silo hypothesis'", Curr Opin Infect Dis 2007 (20,4), pp. 399-407.
Reddehase et al: "CD8-Positive T Lymphocytes Specific for Murine Cytomegalovirus Immediate-Early Antigens Mediate Protective Immunity", Journal of Virology 1987 (61), pp. 3102-3108.
Stanley A. Plotkin: "Cytomegalovirus vaccines", Elsevier 2008, pp. 1147-1154.
Pepperl-Klindworth et al: Current Perspectives in Vaccine Development:, Caister Academic Press LTD 2006, 23 pages.
Pepperl et al: "Dense Bodies of Human Cytomegalovirus Induce both Humoral and Cellular Immune Responses in the Absence of a Viral Gene Expression", Journal of Virology 2000 (74,13), pp. 6132-6146.
Karl S. Peggs: "Cytomegalovirus following stem cell transplantation: from pharmacologic to immunologic therapy", Expert Rev. Anti Infect. Ther 2004 (2,4), pp. 559-573.
Pass et al: "Vaccine Prevention of Maternal Cytomegalovirus Infection", The New England Journal of Medicine, 2009 (360,12)pp. 1191-1199.
Pascolo et al: "HLA-A2.a-restricted Education and Cytolytic Activity of CD8+ T Lymphocytes from B2 Microglobulin (B2m) HLA-A2.1 Monochain Transgenic H-2Db B2m Double Knockout Mice", J Exp. Med. 1997 (185,12), pp. 2043-2051.
Pande et al: "Structural Analysis of a 64-kDa Major Structural Protein of Human Cytomegalovirus (Towne): Identification of a Phosphorylation Site and Comparison to pp65 to HCMV (AD169)", Virology 1990 (178,1), pp. 6-14.
Mwintshi et al: "Prevention and management of cytomegalovirus infection in solid-organ transplantation", Expert Rev. Anti Infect. Ther. 2007 (5,2), pp. 295-304.
Mersseman et al: "Refinement of strategies for the development of a human cytomegalovirus dense body vaccine", Med Microbiol Immunol 2008 (197), pp. 97-107.
Mersseman et al: "Exogenous introduction of an immunodominant peptide from the non-structural IE1 protein of human cytomegalovirus into the MHC class I presentation pathway by recombinant dense bodies", Journal of General Virology 2008 (89), pp. 369-379.
Ljungman et al: "Risk assessment in haematopoietic stem cell transplantation: Viral status", Best Practice & Research Clinical Haematology 2007 (20,2), pp. 209-217.
Irmiere et al: "Isolation and Characterization of a Noninfectious Virion-like Particle Released from Cells Infected with Human Strains of cytomegalovirus", Virology 1983 (130), pp. 118-133.
Hobom et al: "Fast Screening Procedures for Random Transposon Libraries of Cloned Herpesvirus Genomes: Mutational Analysis of Human Cytomegalovirus Envelope Glycoprotein Genes", Journal of Virology 2000 (74,17), pp. 7720-7729.
Herr et al: "Cytomegalovirus and varicella-zoster virus vaccines in hematopoietic stem cell transplantation", Expert Reviews 2009 (8,8), pp. 999-1021.
Einsele et al: "CMV-Specific Immunotherapy", Human Immunology 2004 (65,5), pp. 432-436.
Gallez-Hawkins et al: "Use of Transgenic HLA A*0201/Kb and HHD II Mice to Evaluate Frequency of Cytomegalovirus IE1-Derived Peptide Usage in Eliciting Human CD8 Cytokine Response", J Virol 2003 (77,7), pp. 4457-4462.
Frankenberg et al: "Identification of a Conserved HLA-A2-Restricted Decapetide from the IE1 Protein (pUL123) of Human Cytomegalovirus", Virology 2002 (295), pp. 208-216.
Diamond et al: "Development of a Candidate HLA A*0201 restricted Peptide-Based Vaccine Against Human Cytomegalovirus Infection", Blood 1997 (90,5), pp. 1751-1767.
Cheeran et al: "Neuropathogenesis of Congenital Cytomegalovirus Infection: Disease Mechanisms and Prospects for Intervention", Clin. Microbiol. Rev. 2009 (22,1), pp. 99-126.
Borst et al: "Cloning of the Human Cytomegalovirus (HCMV) Genome as an Infectious Bacterial Artificial Chromosome in *Escherichia coli*: a New Approach for Construction of HCMV Mutants", J. Virol. 1999 (73,10), pp. 8320-8329.
Böhm et al: "The Immune Evasion Paradox: Immunoevasins of Murine Cytomegalovirus Enhance Priming of CD8 T Cells by Preventing Negative Feedback Regulation", J. Virol. 2008 (82,23), pp. 11637-11650.
Boeckh et al: "The impact of cytomegalovirus serostatus of donor and recipient before hematopoietic stem cell transplantation in the era of antiviral prophylaxis and preemptive therapy", Blood 2004 (103,6), pp. 2003-2008.
Boeckh et al: "Cytomegalovirus in Hematopoietic Stem Cell Transplant Recipients: Current Status, Known Challenges, and Future Strategies", Biology of Blood and Marrow Transplant 2003 (9,9), pp. 543-558.
Besold et al: "Immune evasion proteins gpUS2 and gpUS11 of human cytomegalovirus incompletely protect infected cells from CDI T cell recognition", Virology 2009 (391,1), pp. 5-19.
Besold et al: "Processing and MHC class I presentation of human cytomegalovirus pp65-derived peptides persist despite gpUS2-11 mediated immune evasion", Journal of General Virology 2007 (88), pp. 1429-1439.
Bernstein et al: "Randomized, double-blind, Phase 1 trial of an alphavirus replicon vaccine for cytomegalovirus in CMV seronegative adult volunteers", Vaccine 2009 (28,2), pp. 484-493.
Arthurs et al: "Delayed-Onset Primary Cytomegalovirus Disease After Liver Transplantation", Liver Transplantation 2007 (13,12), pp. 1703-1709.
Arthurs et al: "Delayed-Onset Primary Cytomegalovirus disease and the Risk of Allograft Failure and Mortality after Kidney Transplantation", Clinical Infectious Diseases 2008 (46,6), pp. 840-846.

```
mesrgrrcpe misvlgpisg hvlkavfsrg dtpvlphetr llqtfihvrv sqpslilvsq
ytpdstpchr gdnqlqvqht yftgsevenv svnvhnptgr sicpsqepms iyvyalplkm
lnipsinvhh ypsaaerkhr hlpvadavih asgkqmwqar ltvsglawtr qqnqwkepdv
yytsafvfpt kdvalrhvvc ahelvcsmen tratkmqvig dqyvkvyles fcedvpsgkl
fmhvtlgsdv eedltmtrnp qpfmrphern gftvlcpknm iikpgkishi mldvaftshe
hfgllcpksi pglsisgnll mngqqiflev qairetvelr qydpvaalff fdidlllqrg
pqysehptft sqyriqgkle yrhtwdrhde gaaqgdddvw tsgsdsdeel vtterktprv
tgggamagas tsagrkrksa ssatactagv mtrgrlkaes tvapeedtde dsdneihnpa
vftwppwqag ilarnlvpmv atvqgqnlky qeffwdandi yrifaelegv wqpaaqpkrr
rhrqdalpgp ciastpkkhr g
```

Fig. 5

VIRAL PARTICLE RELEASED AFTER INFECTION OF MAMMALIAN CELLS BY HUMAN CYTOMEGALOVIRUS (HCMV) CONTAINING A FUSION PROTEIN AND USE THEREOF

The present invention is related to a viral particle released after infection of mammalian cells by human cytomegalovirus (HCMV), wherein
 a) the particle is surrounded by a lipid membrane in which viral glycoproteins are embedded,
 b) the particle contains neither viral DNA nor capsids; and
 c) the particle contains a fusion protein comprising one or more parts of the T-cell antigen pp65 and at least one heterologous peptide;
and the use of such viral particle or of a plurality of such viral particle.

Infection with the human cytomegalovirus (HCMV) is a major cause of disease in patients following solid organ or haematopoetic stem cell transplantation [1-9]. Furthermore, transmission of the virus during pregnancy is one of the most frequent causes of lasting sequelae in the newborn in the western hemisphere [10; 11]. The development of an HCMV vaccine has thus been identified as a high priority goal [12].

One aim of such vaccine would be to prevent infection in the mother or, at least, cross-placental transmission. Induction of neutralizing antibodies is considered essential to achieve this. In contrast, protection against reactivation and control of infection in transplant recipients is considered to be afforded by cellular responses, particularly mediated through CD8 T cells [13-15]. Therapeutic vaccination of transplant recipients, addressing the lymphocyte response, possibly combined with adoptive T-cell transfer would be desirable to ameliorate the consequences of viral reactivation of HCMV in the post-transplant period [16].

Despite promising approaches to develop an HCMV vaccine, there is however still no licensed formulation available [10; 17-19]. From numerous studies addressing the immune effectors that afford protection, it appears evident that an ideal vaccine against HCMV should induce both antiviral neutralizing antibodies and T lymphocytes [10; 17; 18; 38]. There is, however, concern if such a universal HCMV vaccine may ever be established. A recent clinical study showed that alphavirus replicons expressing HCMV proteins were well tolerated and induced sustained cellular and humoral responses [19]. Another study employed purified gB as vaccine and provided encouraging results, as significant levels of HCMV neutralizing antibodies could be induced [18]. These vaccines hold promise to be used for the prevention of congenital HCMV infection.

In previous studies in mice, the so-called dense bodies, which are also referred to herein as DB, proved to be surprisingly immunogenic [20]. As generally understood in the art and as also used herein a dense body is a viral particle released after infection of mammalian cells by human cytomegalovirus (HCMV), wherein
 a) the particle is surrounded by a lipid membrane in which viral glycoproteins are embedded,
 b) the particle contains neither viral DNA nor capsids.

Preferably such dense body also contains a fusion protein comprising one or more parts of the T-cell antigen pp65 and at least one heterologous peptide. Dense bodies and their preparation are also described in international patent application WO 00/53729.

In view of their surprising immunogenicity, efforts were made to develop DB as an HCMV vaccine. Recent experiments provided experimental evidence that DB can be modified in their antigenic content [21; 22]. This was achieved by expressing a fusion protein consisting of the major DB-component pp65 and a heterologous MHC-class I presented peptide from the viral IE1-protein by a recombinant HCMV. This resulted in the formation of recombinant DB (recDB) in infected human foreskin fibroblasts (HFF). The recDB containing the fusion protein were released from infected HFF [21]. Application of these particles to HLA-A2 transgenic HHD-mice induced a CD8+ T lymphocyte response, which became apparent after in vitro peptide stimulation of isolated T cells [22]. However, HCMV specific T cells could not be immediately detected when CD8+ T cell fractions were tested directly ex-vivo by Elispot analysis. This indicated that, although in principle suitable for therapeutic application, priming was not as prominent as desirable with these particles. Further to that, the yield of these recDB from infected HFF cultures was low.

Therefore, the problem underlying the present invention was to provide a viral dense body which is suitable as a vaccine, wherein the viral dense body contains a fusion protein comprising one or more parts of the T-cell antigen pp65 and at least one heterologous peptide and wherein preferably the vaccine is capable of eliciting an immune response to the at least one heterologous peptide.

A further problem underlying the present invention was to provide a viral dense body, wherein the viral dense body contains a fusion protein comprising one or more parts of the T-cell antigen pp65 and at least one heterologous peptide and wherein preferably the dense body is capable of inducing the formation of neutralizing antibodies and/or a CD8+ T lymphocyte response.

A still further problem underlying the present invention was to provide a viral dense body, wherein the viral dense body contains a fusion protein comprising one or more part of the T-cell antigen pp65 and at least one heterologous peptide and wherein the dense body can be prepared at high yields.

These and other problems are solved by the subject matter of the attached independent claims. Preferred embodiments may be taken from the also attached dependent claims.

More specifically, the problem underlying the present invention is solved in a first aspect which is also the first embodiment of the first aspect, by a viral particle released after infection of mammalian cells by human cytomegalovirus (HCMV), wherein
 a) the particle is surrounded by a lipid membrane in which viral glycoproteins are embedded,
 b) the particle contains neither viral DNA nor capsids; and
 c) the particle contains a fusion protein comprising one or more parts of the T-cell antigen pp65 and at least one heterologous peptide,
and wherein the at least one heterologous peptide is inserted at amino acid position W175 or A534 of the amino acid sequence of the T-cell antigen pp65.

In a second embodiment of the first aspect which is also an embodiment of the first embodiment of the first aspect, the at least one heterologous peptide is inserted at amino acid position W175 of the amino acid sequence of the T-cell antigen pp65.

In a third embodiment of the first aspect which is also an embodiment of the first and the second embodiment of the first aspect, the amino acid sequence of the T-cell antigen pp65 comprises an amino acid sequence according to SEQ ID NO: 1.

In a fourth embodiment of the first aspect which is also an embodiment of the first, the second and the third embodiment of the first aspect, the particle is highly antigenic.

In a fifth embodiment of the first aspect which is also an embodiment of the first, the second, the third and the fourth embodiment of the first aspect, the particle is capable of inducing the formation of neutralizing antibodies.

In a sixth embodiment of the first aspect which is also an embodiment of the first, the second, the third, the fourth and the fifth embodiment of the first aspect, the particle is capable of inducing a $CD8^+$ T lymphocyte response.

In a seventh embodiment of the first aspect which is also an embodiment of the first, the second, the third, the fourth, the fifth and the sixth embodiment of the first aspect, the at least one heterologous peptide is a MHC-class I presented antigen.

In an eighth embodiment of the first aspect which is also an embodiment of the first, the second, the third, the fourth, the fifth, the sixth and the seventh embodiment of the first aspect, the at least one heterologous peptide comprises or is formed of one or more parts of one or more proteins which is/are different from pp65.

In a ninth embodiment of the first aspect which is also an embodiment of the first, the second, the third, the fourth, the fifth, the sixth, the seventh and the eighth embodiment of the first aspect, the at least one heterologous peptide comprises or is one or more parts of an HCMV glycoprotein.

In a tenth embodiment of the first aspect which is also an embodiment of the first, the second, the third, the fourth, the fifth, the sixth, the seventh, the eighth and the ninth embodiment of the first aspect, the at least one heterologous peptide comprises or is one or more parts of the HCMV glycoprotein gB.

In an eleventh embodiment of the first aspect which is also an embodiment of the first, the second, the third, the fourth, the fifth, the sixth, the seventh, the eighth and the ninth embodiment of the first aspect, the at least one heterologous peptide comprises or is one or more parts of the HCMV glycoprotein gH.

In a twelfth embodiment of the first aspect which is also an embodiment of the first, the second, the third, the fourth, the fifth, the sixth, the seventh, the eighth and the ninth embodiment of the first aspect, the at least one heterologous peptide comprises or consists of at least two HCMV glycoproteins which are variants of a particular glycoprotein from different HCMV strains.

In a thirteenth embodiment of the first aspect which is also an embodiment of the twelfth embodiment of the first aspect, one of the at least two variants of the particular glycoprotein is the variant of the HCMV Towne strain and the other of the at least two variants of the particular glycoprotein is the variant of the HCMV Ad169 strain.

In a fourteenth embodiment of the first aspect which is also an embodiment of the twelfth and the thirteenth embodiment of the first aspect, the glycoprotein is the gB protein of HCMV.

In a fifteenth embodiment of the first aspect which is also an embodiment of the first, the second, the third, the fourth, the fifth, the sixth, the seventh and the eighth embodiment of the first aspect, the at least one heterologous peptide comprises or is one or more parts of the HCMV protein IE1.

In a sixteenth embodiment of the first aspect which is also an embodiment of the first, the second, the third, the fourth, the fifth, the sixth, the seventh and the eighth embodiment of the first aspect, the at least one heterologous peptide comprises or is one or more parts of an HCMV glycoprotein and one or more parts of the HCMV protein IE1.

In a seventeenth embodiment of the first aspect which is also an embodiment of the first, the second, the third, the fourth, the fifth, the sixth, the seventh and the eighth embodiment of the first aspect, the at least one heterologous peptide is one or more parts of a protein which is part of a human pathogen other than HCMV.

In an eighteenth embodiment of the first aspect which is also an embodiment of the seventeenth embodiment of the first aspect, the protein which is part of a human pathogen other than HCMV, is a protein against which cytotoxic T lymphocytes are formed in humans upon natural infection of humans with the human pathogen other than HCMV.

In a nineteenth embodiment of the first aspect which is also an embodiment of the eighteenth embodiment of the first aspect, the human pathogen other than HCMV is human pathogen selected from the group comprising HIV-1, HBV, HCV and influenza.

In a twentieth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth and the nineteenth embodiment of the first aspect, the fusion protein is a fusion protein comprising a full-length T-cell antigen pp65 and at least one heterologous peptide.

In a twenty-first embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth and the twentieth embodiment of the first aspect, the viral particle, or a plurality of such a particle, is for the manufacture of a medicament for the treatment and/or prevention of a disease.

In a twenty-second embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth and the twentieth embodiment of the first aspect, the viral particle, or a plurality of such a particle, is for use in a method for the treatment and/or prevention of a disease.

In a twenty-third embodiment of the first aspect which is also an embodiment of the twenty-first and the twenty-second embodiment of the first aspect, the disease is a disease which can be treated and/or prevented by the formation of neutralizing antibodies against the at least one heterologous peptide or a derivative thereof, or by the induction of a $CD8^+$ T lymphocyte response against the at least one heterologous peptide or a derivative thereof.

In a twenty-fourth embodiment of the first aspect which is also an embodiment of the first, the second, the third, the fourth, the fifth, the sixth, the seventh, the eighth, the ninth, the tenth, the twelfth, the thirteenth, the fourteenth, the fifteenth, the sixteenth, the seventeenth, the eighteenth, the nineteenth and the twentieth embodiment of the first aspect, the viral particle, or a plurality of such a particle, is for the manufacture of a vaccine.

In a twenty-fifth embodiment of the first aspect which is also an embodiment of the twenty-fourth embodiment of the first aspect, the vaccine is for the treatment and/or prevention of HCMV infection.

In a twenty-sixth embodiment of the first aspect which is also an embodiment of the twenty-fourth embodiment of the first aspect, the vaccine is for the treatment and/or prevention of side effects of transplantation.

In a twenty-seventh embodiment of the first aspect which is also an embodiment of the twenty-sixth embodiment of the first aspect, the transplantation is transplantation of a solid organ or haematopoetic stem cells.

In a twenty-eighth embodiment of the first aspect which is also an embodiment of the twenty-sixth and the twenty-seventh embodiment of the first aspect, the side effect is caused by or is going along with a HCMV infection.

The problem underlying the present invention is solved in a second aspect which is also the first embodiment of the second aspect, by use of a viral particle according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth and the twentieth embodiment of the first aspect for the manufacture of a medicament for the treatment and/or prevention of a diseases or side effects, whereby the disease or side effects is a disease or are side effects as defined in each and any of the preceding embodiments and of each and any aspect.

The problem underlying the present invention is solved in a third aspect which is also the first embodiment of the third aspect, by use of a viral particle according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth and the twentieth embodiment of the first aspect for the manufacture of a vaccine for the treatment and/or prevention of a disease or side effects, whereby the disease or side effects is a disease or are side effects as defined in each and any of the preceding embodiments and of each and any aspect.

Based on the insight that the insertion site for heterologous peptide sequences into pp65 was critical for the efficiency of subsequent DB formation, the present inventors have surprisingly found that the fusion protein which is contained in the viral particles of the invention and which comprises one or more parts of the T-cell antigen pp65 and at least one heterologous peptide, confers advantageous characteristics to the DB if the heterologous peptide is inserted at amino acid position W 175 or at amino acid position A534 of the pp65 amino acid sequence. The advantageous characteristics of these fusion proteins comprise the induction of neutralizing antibodies against the heterologous peptide, the induction of a $CD8^+$ T lymphocyte response to the heterologous peptide and the production of such DB at a high yield. Furthermore, these two loci in pp65 allowed efficient formation and release of DB containing said fusion proteins. The CD8+ T lymphocyte response observed for these two fusion proteins primed CD8 T cell responses, which are readily detectable by ex vivo Elispot analyses of CD8 T cell fractions.

The T-cell antigen pp65, which is also referred to in the art as UL 83, has been described by Pande, H. et al. (Pande, H, Lee, T. D., Churchill, M. A. and Zaia, J. A, "Structural analysis of a 64-kDa major structural protein of human cytomegalovirus (Towne): identification of a phosphorylation site and comparison to pp65 of HCMV (AD169); Virology 178 (1), 6-14 (1990)).

Little is known about the function of pp65 and about domains, important for function and proper folding of the protein. Consequently, there is no rationale for insertion site selection that would definitely spare functionally relevant regions within pp65. Insertion site selection was performed in a way to avoid regions conserved in beta-herpesviruses and also predicted secondary structures (α-helices and β-sheets). This was done assuming that conserved regions, α-helices and β-sheets could be structurally and functionally important and should not be destroyed. However, most of these mutants failed to efficiently form recDB, indicating that this strategy could not identify proper insertion sites. In the light thereof the present inventors surprisingly found that the insertion sites in RV-SB3 and RV-SB6 proved to be more appropriate for recDB formation.

As is shown in the present application exogenous introduction of chimeric pp65 by DB-SB3 and DB-SB6 into HFF led to efficient presentation of pp65NLV and IEITMY. Application of these particles to HLA-A2 transgenic HI-ID mice primed a CD8 T cell response against both peptides that could be detected after in-vitro expansion of these T cells with the cognate peptide. Similar results have also been obtained in previous experiments, using recDB with insertion of the IE1-peptide at position 548 of pp65 [21; 22]. However, using the latter recDB, CD8 T cells against either peptide were undetectable directly ex vivo, suggesting that priming was inefficient. Application of DB-SB3, in contrast, led to readily detectable frequencies of pp65NLV-specific and IE1TMY-specific CD8 T cells. This indicates that these recDB were highly immunogenic and induced T cells against both the endogenous and the heterologous peptide.

In an embodiment of the invention the heterologous peptide is an antigenic peptide and more preferably an antigenic heterologous peptide.

In an embodiment of the present invention that the heterologous peptide is different from the IE1 protein of HCMV or a part thereof.

In an embodiment of the present invention the length of a peptide is from about 4 to 40 amino acid residues, preferably about 6 to 25 amino acid residues and more preferably about 8 to 15 amino acid residues and most preferably about 8-12 amino acid residues.

As preferably used, any wording which specifies the limits of a range such as, e.g., "from 1 to 5" means any integer from 1 to 5, i.e. 1, 2, 3, 4 and 5. In other words, any range that is defined by two integers comprises both the two integers defining said limits of the definition and any integer comprised by or contained within said range.

In an embodiment of the present invention the antigenicity of the viral particle of the invention is increased compared to the dense bodies of the prior art, more specifically those dense bodies where the dense body contains a fusion protein comprising the full-length T-cell antigen pp65.

In an embodiment of the present invention the formation of the viral particle of the invention is increased compared to the formation of dense bodies as described in [25].

It will be acknowledged by a person skilled in the art that, preferably, the HCMV protein IE1 is also referred to as ppUL 123.

It will also be acknowledged that the fusion protein contained in the particle is, in a preferred embodiment a chimeric protein.

The present invention is now further illustrated by reference to the following figures and examples from which further advantages, features, and embodiments may be taken, wherein FIG. 1 shows the result of an indirect immuno fluorescence analysis of HFF, infected with HCMV recombinants;

FIG. 5 shows the amino acid sequence of full-length pp65 (SEQ ID NO:1)

Figure 1:
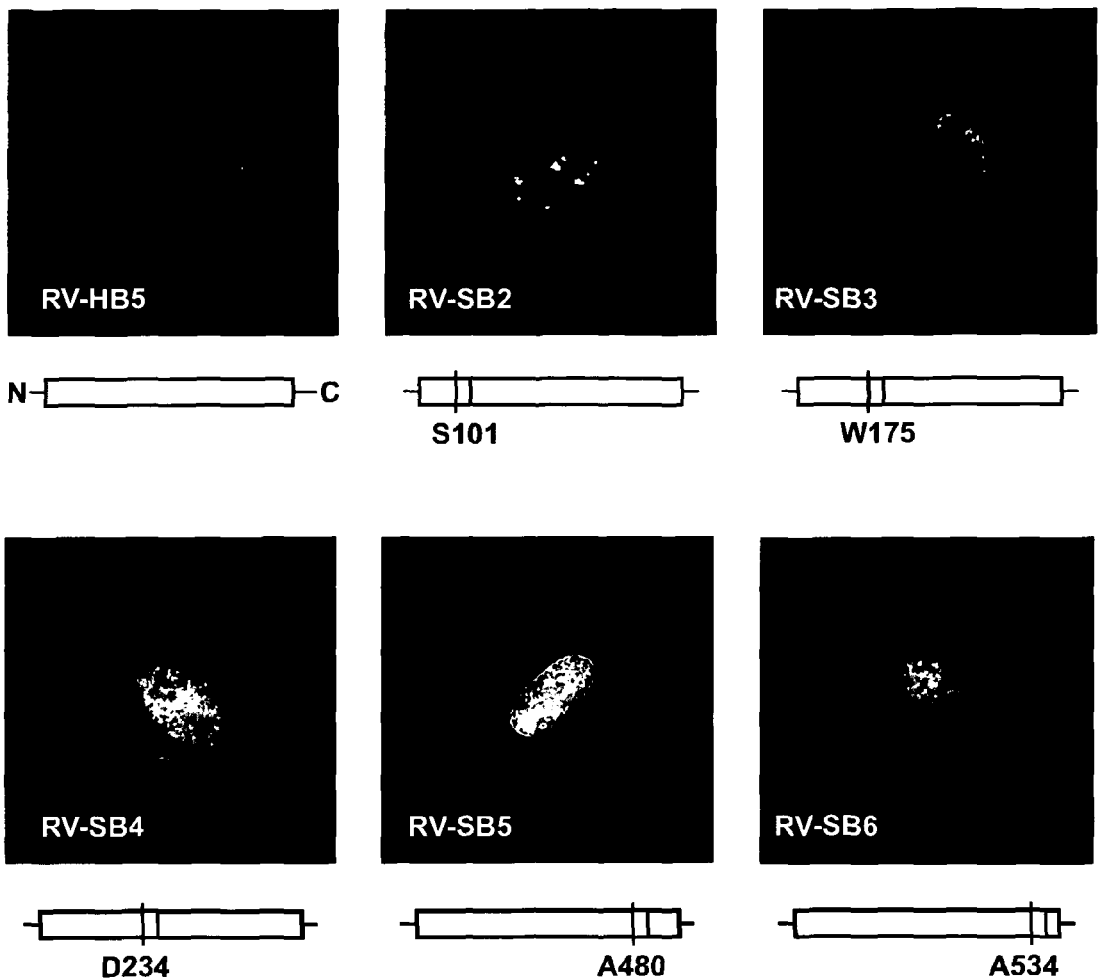

FIG. 1 shows the result of an indirect immuno fluorescence analysis of HFF, infected with HCMV recombinants. Cells were infected with the indicated viruses for four days and were subsequently processed for immuno flourescence analysis. The configuration of the recombinant pp65, expressed by each virus is indicated below the micrographs. The N-terminal amino acid of pp65, flanking the insertion site is denoted.

Figure 2:
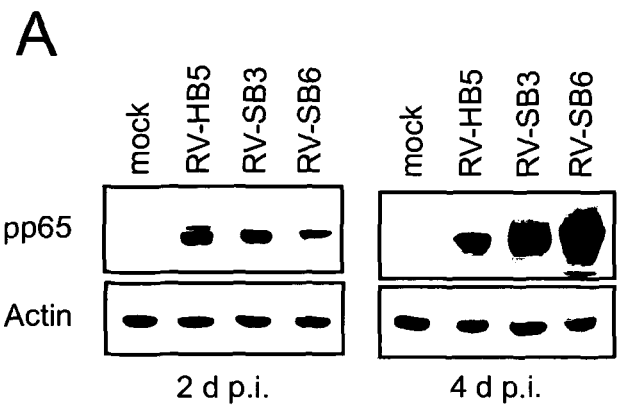
FIG. 2 shows the result of an immuno blot analysis (A), the result of a quantitative DNA-PCR analysis as a diagram indicating genome copies/ml as a function of time (d.p.i) for various fusion proteins (B), and the result of a further immuno blot analysis (C)
Figure 2:
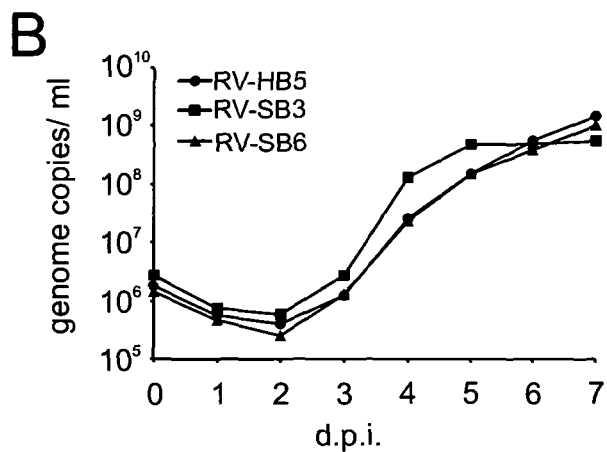
Figure 2:
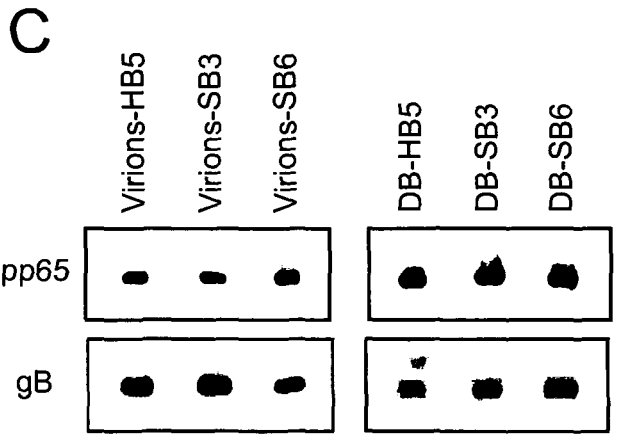

FIG. 2 shows the expression of pp65-fusion proteins, replication of recombinant viruses and efficiency of packaging of fusion proteins into virions and DB. (A), Immuno blot analysis of 1- and 4-day infected HFF. Cells were infected at an m.o.i. of 2 and were collected at the indicated times for analysis. Filters were probed with pp65-specific monoclonal antibody 65-33. Amounts of proteins in each lane were normalized against β-actin. (B), Quantitative DNA-PCR analysis of viral genomes in the cell culture supernatant of infected HFF. Cells were infected at an m.o.i. of 10 genomes/cell. Culture supernatants were collected at the indicated time points and frozen. PCR analysis was performed in parallel in the same assay. (C), Immunoblot analysis of pp65, packaged in recDB or virions. Cells were infected with the recombinant viruses or with wt RV-HB5 for 6-7 days. Supernatants were subjected to glycerol-tartrate gradient centrifugation to collect virions- and DB-fractions. These fractions were analyzed by immunoblot, using monoclonal antibody 65-33 or, as internal standard, using a monoclonal antibody against viral gB.

Figure 3:
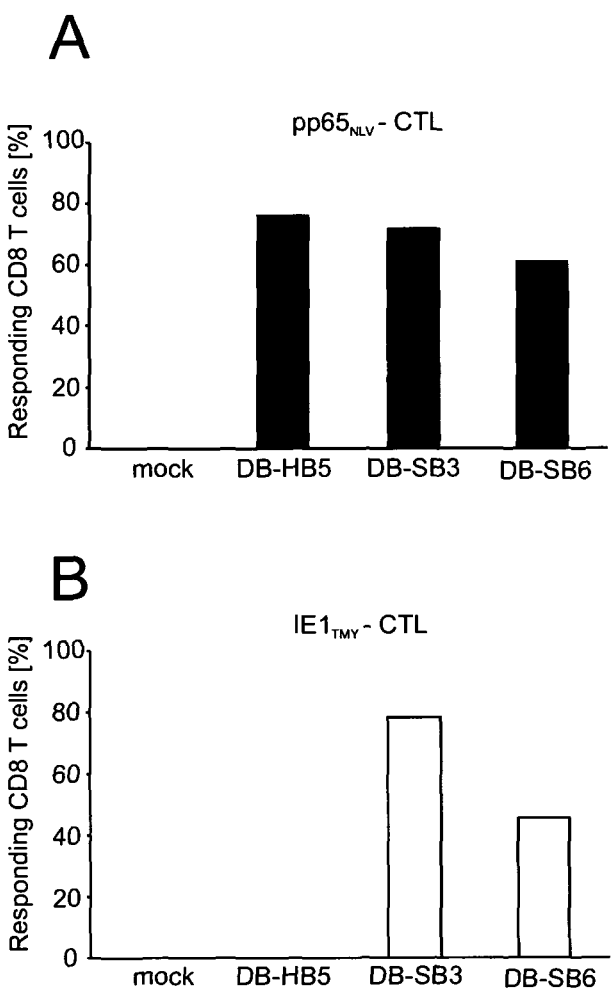
FIG. 3 shows the result of an IFN-γ-Elispot analysis as a diagram indicating the percentage of responding $CD8^+$ cells for various fusion proteins either using either pp65NLV-CTL (A) or IE1TMY-CTL (B) as responder cells.

FIG. 3 shows the result of an IFN-γ-Elispot analysis of MHC-class I presentation by HLA-A2 positive HFF, treated with recDB. Cells were treated with the indicated DB and were subsequently used as stimulator cells in IFN-γ-Elispot analysis, using either pp65NLV-CTL (A) or IE1TMY-CTL (B) as responder cells.

Figure 4:
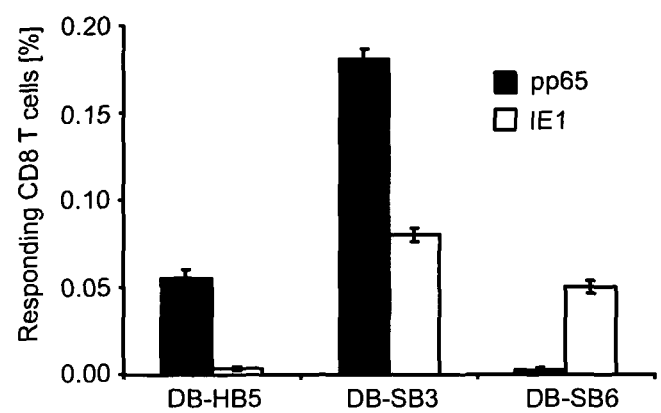
FIG. 4 shows the result of an IFN-γ-Elispot analysis as a diagram indicating the percentage of responding CD8+ cells for various fusion proteins either using RMA-S cells as stimulator cells.

FIG. 4 shows the result of an ex vivo IFN-γ-Elispot analysis of CD8+ enriched spleen cells from HHD-mice, immunized with recDB. RMA-S cells, loaded with the cognate peptides were taken as stimulator cells. Bar sizes represent most probable frequencies of IFN-γ secreting CD8 T cells, as determined by linear regression analysis, described by Böhm et al [37]. Error bars indicate 95% confidence intervals.

EXAMPLE 1

Materials and Methods

1. Cells

Primary human foreskin fibroblasts, CTL lines and T2 cells were cultured as described before [23]. RMA-S cells [24] were grown in RPMI 1640 medium (PAA Laboratories, Cölbe, Germany) supplemented with 10% FCS, 2 mM L-glutamine, 50 mg gentamicin L-1 and 5 µM β-mercaptoethanol.

2. Plasmids and Viruses

For mutagenesis of the viral DNA, the HCMV bacterial artificial chromosome (BAC) pHB5 [25] was used. Mutagenesis of pHB5 was performed according to the galK positive/negative selection procedure [26] as described elsewhere [21]. The DNA sequence inserted into the UL83 open reading frame encoded the HLA-A2 presented peptide IE1TMY [IE1297-305], flanked by additional amino acids to enable accurate proteasomal processing. The additional polypeptide fused to pp65 reads TSDACMMTMYGG-ISLLSEFC, with the HLA-A2 presented nonapeptide being underlined. Viral reconstitution from BAC clones was performed according to Hobom et al. [27]. The disclosed amino acid sequence is identified as SEQ ID NO:2 in the sequence listing.

Virus stocks were generated, titrated and quantified either by counting IE1 positive cells at 48 hours p.i. or by TaqMan DNA PCR analysis of extracellular viral genomes as described [28]. HFF were infected for 7 days. Infection at a moi of 0.1 resulted in a number of roughly 10 intracellular viral genomes.

3. Dense Body Purification, Indirect Immunofluorescence Analysis and Immunoblotting DB were purified from late-stage infected HFF by glycerol-tartrate gradient ultracentrifugation as originally published by Irmiere and Gibson [29] and described previously [20]. Indirect immunofluorescence analysis was carried out as described [30]. The pp65 was labelled by using monoclonal antibody 65-33 (kindly provided by W. Britt, University of Alabama, Birmingham, Ala., USA) and FITC-conjugated secondary antibodies (DAKO, Hamburg, Germany). The nucleus was counterstained with DAPI. Data from immunofluorescence analyses were collected using an Axiophot-1 microscope (Zeiss) at magnification of 1000 fold. For immunoblotting, protein samples were denatured under reducing conditions, separated by SDS-PAGE and transferred onto nitrocellulose membranes (Millipore, Schwalbach, Germany) by electroblotting at 400 mA for 1 h 45 min. The membranes were incubated with antibodies against pp65, β-actin (Rockland, Gilbertsville, Pa., USA) and glycoprotein B (gB) [31]). Western blots were probed with anti-mouse or anti-rabbit secondary antbodies, conjugated to ALEXA Fluor 680 (Invitrogen, Karlsruhe, Germany) or IRdye 800 (Rockland). Blotted proteins were detected and quantified using the Odyssey infrared imaging system (LI-COR, Lincoln, Nebr., USA).

2.4 Interferon γ-Elispot Assay of HFF Incubated with recDB

Enzyme linked immunospot (Elispot) assays were performed as described before [23; 32]. CTL lines specific for the HLA-A0201 (A2) restricted HCMV-derived peptides pp65495-503 (pp65NLV-CTL) [33; 34] and IE1297-305 (IE1TMY-CTL) [35] were used in these analyses. The CTL lines had been generated by immunizing HLA-A2/huCD8 double-transgenic (tg) mice [23].

2.5 HLA-A2 Transgenic Mouse Model 8-12 week-old HLA-A2 transgenic mice (HHD mice, [36]) were immunized intraperitoneally with 6 µg DB of RV-HB5 (DB-HB5), RV-SB3 (DB-SB3) or RV-SB6 (DB-SB6), respectively, or with PBS. Lymphocytes were prepared from the spleens at day 7 after immunization. CD8 T cells were enriched by MACS sorting and the frequency of IFN-γ secreting cells was analysed by Elispot directly ex vivo, using peptide loaded RMA-S HHD or T2 stimulator cells. In this setting the Elispot plates from Millipore (Schwalbach/Ts., Germany) were used. The Elispot assay was performed according to the manufacturer's recommendations. Frequencies of responding cells were determined by linear regression analysis as described by Böhm et al [37].

EXAMPLE 2

Insertion Site Selection is Critical for Formation of Cytoplasmic DB

As will be illustrated in this example, selection of the insertion site of the heterologous peptide is critical for formation of cytoplasmic DB.

The potential of a vaccine candidate to be further developed critically depends on the yield that can be achieved for further up-scaling. In previous work, proof could be provided that DB can be modified in their antigenic content by fusing a heterologous peptide sequence to the tegument protein pp65 [21]. However, cells infected with the respective recombinant of HCMV released only limited amounts of recDB. Therefore the hypothesis was tested that insertion of heterologous sequence such as the amino acid sequence of a heterologous peptide at other sites within pp65 would enhance the yield of recDB.

Five sites in different portions of the molecule were selected for insertion (FIG. 1). The inserted peptide consisted of 20 amino acids encompassing the HLA-A2 presented nonapeptide TMYGGISLL (IE1TMY) from the HCMV IE1 protein [35]. Recombinant viruses were generated by modifying the HCMV BAC plasmid pHB5 [25], using the galK-based selection procedure [21; 22]. Recombinant BAC-plasmids were analyzed for accuracy by restriction endonuclease digestion and nucleotide sequencing of the insertion site (data not shown). Reconstitution of recombinant viruses was subsequently performed by transfection of the BAC-plasmids into HFF. The resulting viruses were tested for DB formation. One hallmark of HCMV infection of HFF is the cytoplasmic accumulation of DB, which can be visualized by indirect immuno fluorescence analysis (IFA). Consequently, HFF were infected with the newly generated mutants and IFA was performed at 4 days post infection (d.p.i.), using a pp65-specific antibody (FIG. 1). Only cells infected with the mutants RV-SB3 and RV-SB6 showed the formation of cytoplasmic DB in a way comparable to the formation of DB in parental-virus infected cells. In contrast, no or only little DB formation was seen in RV-SB2, RV-SB4, and RV-SB5 infected cells. Note that in these cells, the nucleo-cytoplasmic translocation of pp65, which is typically seen in late-stage infected HFF was impaired. These results indicated that site selection for insertion of heterologous peptide sequences within pp65 was critical for recDB formation. Based on the IFA-results the viruses RV-SB3 and RV-SB6 were chosen for further analysis.

EXAMPLE 3

Comparing RV-SB3 and RV-SB6 with the Parental Strain

As will be shown in this example, recombinant viruses RV-SB3 and RV-SB6 are comparable to the parental strain with respect to pp65-expression, virion release and packaging of pp65 into particles.

Expression levels of pp65 in RV-SB3- and RV-SB6-infected HFF were tested by immunoblot analysis. Cells were infected with either virus or with parental RVHB5 for two or four days, respectively. Cells lysates were subjected to quantitative immunoblot analysis, using the Odyssey infrared imaging system. The amount of cellular actin was taken as internal standard (FIG. 2A). Expression levels of pp65-fusion proteins in RV-SB3- and RV-SB6-infected cells was reduced at 2 days p.i., compared to levels of pp65 in cells infected with parental RV-HB5.

However, at 4 days p.i., the levels of the two fusion proteins appeared to be even higher as that of the pp65 in RV-HB5 infected cells. This indicated that sufficient protein was synthesized in RV-SB3- and RV-SB6-infected cells to direct the synthesis of recDB.

To test the capacity of the recombinant strains to replicate in HFF, cells were infected at an m.o.i. of 0.1, resulting in 10 genome copies/cell and culture supernatant was collected in daily intervals until 7 days p.i. Viral DNA released into the supernatant was quantified using quantitative PCR analysis (FIG. 2B). Both RV-SB3 and RV-SB6 proved to replicate to similar levels as parental RV-HB5.

Packaging of the fusion proteins was finally analyzed by immunoblot analysis of purified virions and DB, collected from infected HFF supernatants by glycerol gradient centrifugation. In this case, normalization was performed using the viral envelope glycoprotein B (gB) as internal standard. No differences in the packaging of pp65 into virions or DBs were found when the recombinant strains were compared to their parental strain (FIG. 2C). Taken together these results indicated that both RV-SB3 and RVSB6 were comparable to RV-HB5 in expression and packaging of pp65 and in replication in infected cells.

EXAMPLE 4

Expression of Both pp65NLV and IE1TMY by DB-SB3- or DB-SB6-Treated HFF

The present example shows that both pp65NLV and IE1TMY are presented by DB-SB3- or DB-SB6-treated HFF.

One goal of using recDB for vaccine development would be to support cytotoxic T cell reconstitution in patients following transplantation. These cells have been shown to be of critical importance for the prevention of viral reactivation and disease ([13; 15] reviewed in [16]). It thus tested whether the recDB were capable to introduce both the pp65-derived pp65NLV and the IE1-derived IE1TMY into the MHC-class I presentation pathway of HFF.

Accordingly, cells were treated with recDB and were subsequently subjected to interferon-γ Elispot analysis (FIG. 3). As responder cells, CTL clones against both peptides (pp65NLV-CTL; IE1TMY-CTL) were used [23]. Both DB-SB3- and DB-SB6-treated cells presented IE1TMY and pp65NLV. The pp65NLV-presentation was comparable between recDB and wt-DB, indicating that the insertion of the IE1-derived sequence did not impair pp65-presentation in HFF. Treatment of cells with DB-SB3 led to numbers of responding IE1TMY-CTL to levels that were comparable to the pp65-specific response. However, treatment of cells with DB-SB6 led to a markedly reduced number of positive spots in the IE1-specific assay. This indicated that the ability of HFF to present the IE1-peptide after DB incubation was sensitive to the site, where the peptide was inserted into pp65.

EXAMPLE 5

Immunization with Recombinant DB (recDB) Results in IE1TMY-Specific and pp65NLV-Specific CD8 T Cells This example shows that immunization with recombinant DB (recDB) primes significant frequencies IE1TMY-specific and pp65NLV-specific CD8 T cells.

Previous experiments had shown that recDB could induce IE1TMY-specific CD8 T cells in mice. These cells were, however, only detectable after in-vitro stimulation of CD8 T cell fractions from immunized mice with the cognate peptide. No responding CD8 T cells were detected directly ex-vivo, indicating that the total number of specific cells, and thus the overall response to those recDB was low [21]. To evaluate the immunological potential of the newly established recDB, HLA-A2 transgenic HHD-mice were immunized with the different DB in the absence of adjuvant. As expected, responding CD8 T cells specific for IE1TMY or pp65NLV were detectable after in-vitro stimulation (data not shown).

Cells from immunized mice were also tested directly ex-vivo. For this, the $CD8^+$ fractions of spleen cells were separated by MACS-sorting and tested in Elispot analysis, using peptide loaded antigen presenting cells. CD8 T cells, specific for IE1TMY could be detected after immunization with both DB-SB3 and DB-SB6 (FIG. 4). The IE1-specific response primed by DB-SB3 appeared be stronger than the response induced by DB-SB6, but both reached clearly detectable levels.

After immunization with DB-SB3, CD8 T cells reactive against the pp65NLV could be detected to a roughly three-fold level, compared to wt-DB.

Surprisingly, however, this response was undetectable in the experimental setting chosen after immunization with DB-SB6 and a pp65NLV-specific response could not be detected ex vivo. This result was confirmed in a second experiment and indicated that the CD8 T cell response, primed against the immunodominant pp65NLV-peptide by immunizing with DB-SB6 was inefficient. (FIG. 4). Comparable results were obtained when T2 cells were chosen for antigen presentation (data not shown). Furthermore, this indicates that these cells were induced in only low frequencies below the detection limit of the assay. In accordance therewith, restimulation of pp65NLV-specific T cells in vitro was delayed compared to IE1TMY-specific cells (data not shown).

Taken together these experiments particularly proved the potential of DB-SB3 to prime a CD8 T cell response against a heterologous antigenic peptide.

LIST OF REFERENCES

In the instant application it is referred to the various references as follows:

[1] Mwintshi K, Brennan D C. Prevention and management of cytomegalovirus infection in solid-organ transplantation. Expert Rev Anti Infect Ther 2007; 5(2):295-304.
[2] Rubin R H. The pathogenesis and clinical management of cytomegalovirus infection in the organ transplant recipient: the end of the 'silo hypothesis'. Curr Opin Infect Dis 2007; 20(4):399-407.
[3] Arthurs S K, Eid A J, Pedersen R A, Dierkhising R A, Kremers W K, Patel R, et al. Delayed-onset primary cytomegalovirus disease after liver transplantation. Liver Transpl 2007; 13(12):1703-9.
[4] Arthurs S K, Eid A J, Pedersen R A, Kremers W K, Cosio F G, Patel R, et al. Delayed-onset primary cytomegalovirus disease and the risk of allograft failure and mortality after kidney transplantation. Clin Infect Dis 2008; 46(6): 840-6.
[5] Peggs K S. Cytomegalovirus following stem cell transplantation: from pharmacologic to immunologic therapy. Expert Rev Anti Infect Ther 2004; 2(4):559-73.
[6] Hebart H, Einsele H. Clinical aspects of CMV infection after stem cell transplantation. Hum Immunol 2004; 65(5):432-6.
[7] Ljungman P. Risk assessment in haematopoietic stem cell transplantation: viral status. Best Pract Res Clin Haematol 2007; 20(2):209-17.
[8] Boeckh M, Nichols W G, Papanicolaou G, Rubin R, Wingard J R, Zaia J. Cytomegalovirus in hematopoietic stem cell transplant recipients: Current status, known challenges, and future strategies. Biol Blood Marrow Transplant 2003; 9(9):543-58.
[9] Boeckh M, Nichols W G. The impact of cytomegalovirus serostatus of donor and recipient before hematopoietic stem cell transplantation in the era of antiviral prophylaxis and preemptive therapy. Blood 2004; 103(6):2003-8.
[10] Plotkin S A. Cytomegalovirus vaccines. In: Plotkin S A, Orenstein W A, Offit P A, editors. Vaccines. 5 ed. Elsevier, 2008: p. 1147-54.
[11] Cheeran M C, Lokensgard J R, Schleiss M R. Neuropathogenesis of congenital cytomegalovirus infection: disease mechanisms and prospects for intervention. Clin Microbiol Rev 2009; 22(1):99-126, Table.
[12] Stratton K R, Durch J S, Lawrence R. S. Vaccines for the 21st Century. A Tool for Decisionmaking. Washington, D.C.: National Academy Press, 2001.
[13] Reddehase M J, Mutter W, Munch K, Bullring H J, Koszinowski U H. CD8-positive T lymphocytes specific for murine cytomegalovirus immediate-early antigens mediate protective immunity. J Virol 1987; 61:3102-8.
[14] Wills M R, Carmichael A J, Sissons J G. Adaptive Cellular Immunity to Human Cytomegalovirus. In: Reddehase M J, editor. Cytomegalovirus: Molecular Biology and Immunology. Caister Academic Press, Wymondham, Norfolk, U. K., 2006: p. 341-65.
[15] Walter E A, Greenberg P D, Gilbert M J, Finch R J, Watanabe K S, Thomas E D, et al. Reconstitution of cellular immunity against cytomegalovirus in recipients of allogeneic bone marrow by transfer of T-cell clones from the donor. N Engl J Med 1995; 333(16):1038-44.
[16] Herr W, Plachter B. Cytomegalovirus and varicella-zoster virus vaccines in hematopoietic stem cell transplantation. Expert Rev Vaccines 2009; 8(8):999-1021.
[17] Schleiss M R. Cytomegalovirus vaccine development. Curr Top Microbiol Immunol 2008; 325:361-82.
[18] Pass R F, Zhang C, Evans A, Simpson T, Andrews W, Huang M L, et al. Vaccine prevention of maternal cytomegalovirus infection. N Engl J Med 2009; 360(12):1191-9.
[19] Bernstein D I, Reap E A, Katen K, Watson A, Smith K, Norberg P, et al. Randomized, double-blind, Phase 1 trial of an alphavirus replicon vaccine for cytomegalovirus in CMV seronegative adult volunteers. Vaccine 2009; 28(2): 484-93.
[20] Pepperl S, Münster J, Mach M, Harris J R, Plachter B. Dense bodies of human cytomegalovirus induce both humoral and cellular immune responses in the absence of viral gene expression. J Virol 2000; 74(13):6132-46.
[21] Mersseman V, Besold K, Reddehase M J, Wolfrum U, Strand D, Plachter B, et al. Exogenous introduction of an immunodominant peptide from the nonstructural IE1 protein of human cytomegalovirus into the MHC class I presentation pathway by recombinant dense bodies. J Gen Virol 2008; 89 (Pt2):369-79.
[22] Mersseman V, Bohm V, Holtappels R, Deegen P, Wolfrum U, Plachter B, et al. Refinement of strategies for the development of a human cytomegalovirus dense body vaccine. Med Microbiol Immunol 2008; 197(2):97-107.

[23] Besold K, Frankenberg N, Pepperl-Klindworth S, Kuball J, Theobald M, Hahn G, et al. Processing and MHC class I presentation of human cytomegalovirus pp65-derived peptides persist despite gpUS2-11-mediated immune evasion. J Gen Virol 2007; 88(Pt 5):1429-39.

[24] Townsend A, Ohlen C, Bastin J, Ljunggren H G, Foster L, Kure K. Association of class I major histocompatibility heavy and light chains induced by viral peptides. Nature 1989; 340(6233):443-8.

[25] Borst E M, Hahn G, Koszinowski U H, Messerle M. Cloning of the human cytomegalovirus (HCMV) genome as an infectious bacterial artificial chromosome in *Escherichia coli*: a new approach for construction of HCMV mutants. J Virol 1999; 73(10):8320-9.

[26] Warming S, Costantino N, Court D L, Jenkins N A, Copeland N G. Simple and highly efficient BAC recombineering using galK selection. Nucleic Acids Res 2005; 33(4):e36.

[27] Hobom U, Brune W, Messerle M, Hahn G, Koszinowski U H. Fast screening procedures for random transposon libraries of cloned herpesvirus genomes: mutational analysis of human cytomegalovirus envelope glycoprotein genes. J Virol 2000; 74(17):7720-9.

[28] Besold K, Wills M, Plachter B. Immune evasion proteins gpUS2 and gpUS11 of human cytomegalovirus incompletely protect infected cells from CD8 T cell recognition. Virology 2009; 391(1):5-19.

[29] Irmiere A, Gibson W. Isolation and characterization of a noninfectious virionlike particle released from cells infected with human strains of cytomegalovirus. Virology 1983; 130:118-33.

[30] Schmolke S, Drescher P, Jahn G, Plachter B. Nuclear targeting of the tegument protein pp65 (UL83) of human cytomegalovirus: an unusual bipartite nuclear localization signal functions with other portions of the protein to mediate its efficient nuclear transport. J Virol 1995; 69:1071-8.

[31] Utz U, Britt W, Vugler L, Mach M. Identification of a neutralizing epitope on glycoprotein gp58 of human cytomegalovirus. J Virol 1989; 63:1995-2001.

[32] Frankenberg N, Pepperl-Klindworth S, Meyer R G, Plachter B. Identification of a conserved HLA-A2-restricted decapeptide from the IE1 protein (pUL123) of human cytomegalovirus. Virology 2002; 295(2):208-16.

[33] Wills M R, Carmichael A J, Mynard K, Jin X, Weekes M P, Plachter B, et al. The human cytotoxic T-lymphocyte (CTL) response to cytomegalovirus is dominated by structural protein pp65: frequency, specificity, and T-cell receptor usage of pp65-specific CTL. J Virol 1996; 70:7569-79.

[34] Diamond D J, York J, Sun J Y, Wright C L, Forman S J. Development of a candidate HLA A*0201 restricted peptide-based vaccine against human cytomegalovirus infection. Blood 1997; 90(5): 1751-67.

[35] Gallez-Hawkins G, Villacres M C, Li X, Sanborn M C, Lomeli N A, Zaia J A. Use of transgenic HLA A*0201/Kb and HHD II mice to evaluate frequency of cytomegalovirus IE1-derived peptide usage in eliciting human CD8 cytokine response. J Virol 2003; 77(7):4457-62.

[36] Pascolo S, Bervas N, Ure J M, Smith A G, Lemonnier F A, Perarnau B. HLAA2.1-restricted education and cytolytic activity of CD8(+) T lymphocytes from beta2 microglobulin (beta2m) HLA-A2.1 monochain transgenic H-2 Db beta2m double knockout mice. J Exp Med 1997; 185(12):2043-51.

[37] Böhm V, Simon C O, Podlech J, Seckert C K, Gendig D, Deegen P, et al. The immune evasion paradox: immunoevasins of murine cytomegalovirus enhance priming of CD8 T cells by preventing negative feedback regulation. J Virol 2008; 82(23):11637-50.

[38] Pepperl-Klindworth S, Plachter B. Current perspectives in vaccine development. In: Reddehase M J, editor. Cytomegaloviruses: Molecular Biology and Immunology. Caister Academic Press Ltd, Wymondham, Norfolk, U. K., 2006.

The features of the present invention disclosed in the specification, the claims, the sequence listing and/or the drawings may both separately and in any combination thereof be material for realizing the invention in various forms thereof.

The invention claimed is:

1. A viral particle released after infection of mammalian cells by human cytomegalovirus (HCMV), wherein
   a) the particle is surrounded by a lipid membrane in which viral glycoproteins are embedded,
   b) the particle contains neither viral DNA nor capsids; and
   c) the particle contains a fusion protein comprising one or more parts of the T-cell antigen pp65 and at least one heterologous peptide,
   and wherein the at least one heterologous peptide is inserted at amino acid position W175 or A534 of the amino acid sequence of the T-cell antigen pp65, and wherein W175 and A534 correspond to positions 175 and 534 of SEQ ID NO:1.

2. The viral particle according to claim 1, wherein the at least one heterologous peptide is inserted at amino acid position W175 of the amino acid sequence of the T-cell antigen pp65.

3. The viral particle according to claim 1, wherein the amino acid sequence of the T-cell antigen pp65 comprises an amino acid sequence according to SEQ ID NO: 1.

4. The viral particle according to claim 1, wherein the particle is antigenic.

5. The viral particle according to claim 1, wherein the particle is capable of inducing a CD8+T lymphocyte response and wherein the at least one heterologous peptide is a MHC-class I presented antigen.

6. The viral particle according to claim 1, wherein the at least one heterologous peptide comprises or is formed of one or more parts of one or more proteins which are different from pp65.

7. The viral particle according to claim 1, wherein the at least one heterologous peptide comprises or is one or more parts of an HCMV glycoprotein.

8. The viral particle according to claim 1, wherein the at least one heterologous peptide comprises or is one or more parts of the HCMV glycoprotein gB.

9. The viral particle according to claim 1, wherein the at least one heterologous peptide comprises or is one or more parts of the HCMV glycoprotein gH.

10. The viral particle according to claim 1, wherein the at least one heterologous peptide comprises or consists of at least two HCMV glycoproteins which are variants of a glycoprotein from different HCMV strains.

11. The viral particle according to claim 10, wherein one of the at least two variants of the particular glycoprotein is the variant of the HCMV Towne and the other is the variant of the HCMV Ad169.

12. The viral particle according to claim 10, wherein the glycoprotein is the gB protein of HCMV.

13. The viral particle according to claim 1, wherein the at least one heterologous peptide comprises or is one or more parts of the HCMV protein IE1.

14. The viral particle according to claim 1, wherein the at least one heterologous peptide comprises or is one or more parts of an HCMV glycoprotein and one or more parts of the HCMV protein IE1.

15. The viral particle according to claim 1, wherein the at least one heterologous peptide is one or more parts of a protein which is part of a human pathogen other than HCMV.

16. The viral particle according to claim 15, wherein the protein which is part of a human pathogen other than HCMV, is a protein against which cytotoxic T lymphocytes are formed in humans upon natural infection of humans with the human pathogen other than HCMV.

17. The viral particle according to claim 16, wherein the human pathogen other than HCMV is a human pathogen selected from the group consisting of HIV-1, HBV, HCV and influenza.

18. The viral particle according to claim 1, wherein the fusion protein is a fusion protein comprising a full-length T-cell antigen pp65 and at least one heterologous peptide.

19. A method for the treatment of a disease and/or side effects in a patient, comprising:
providing a medicament comprising a viral particle released after infection of mammalian cells by human cytomegalovirus (HCMV), wherein
a) the viral particle is surrounded by a lipid membrane in which viral glycoproteins are embedded,
b) the viral particle contains neither viral DNA nor capsids, and
c) the viral particle contains a fusion protein comprising one or more parts of the T-cell antigen pp65 and at least one heterologous peptide, wherein the at least one heterologous peptide is inserted at amino position W175 or A534 of the amino acid sequence of the T-cell antigen pp65, wherein W175 and A534 correspond to positions 175 and 534 of SEQ ID NO:1, wherein the treated disease comprises a disease which can be treated by the formation of neutralizing antibodies against the at least one heterologous peptide or a derivative thereof, or by the induction of a CD8+T lymphocyte response against the at least one heterologous peptide or a derivative thereof, and wherein the treated side effects are caused by, or are going along with, a HCMV infection;

administering the medicament to the patient; and treating the disease and/or side effects.

20. A method for the treatment of a disease and/or side effects in a patient, comprising:

providing a vaccine comprising a viral particle released after infection of mammalian cells by human cytomegalovirus (HCMV), wherein a) the viral particle is surrounded by a lipid membrane in which viral glycoproteins are embedded, b) the viral particle contains neither viral DNA nor capsids, and c) the viral particle contains a fusion protein comprising one or more parts of the T-cell antigen pp65 and at least one heterologous peptide, wherein the at least one heterologous peptide is inserted at amino position W175 or A534 of the amino acid sequence of the T-cell antigen pp65, wherein W175 and A534 correspond to positions 175 and 534 of SEQ ID NO:1, wherein the treated disease comprises a disease which can be treated by the formation of neutralizing antibodies against the at least one heterologous peptide or a derivative thereof, or by the induction of a CD8+T lymphocyte response against the at least one heterologous peptide or a derivative thereof, and wherein the treated side effects are caused by, or are going along with, a HCMV infection;

administering the vaccine to the patient; and treating the disease and/or side effects.

* * * * *

SEQUENCE LISTING

<160> NUMBER OF SEQ ID NOS: 2

<210> SEQ ID NO 1
<211> LENGTH: 561
<212> TYPE: PRT
<213> ORGANISM: Human cytomegalovirus

<400> SEQUENCE: 1

```
Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
                20                  25                  30

Pro Val Leu Pro His Glu Thr Arg Leu Leu Gln Thr Phe Ile His Val
            35                  40                  45

Arg Val Ser Gln Pro Ser Leu Ile Leu Val Ser Gln Tyr Thr Pro Asp
        50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95
```

```
Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser Ser
            420                 425                 430

Ala Gly Arg Lys Arg Lys Ser Ala Ser Ser Ala Thr Ala Cys Thr Ala
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
```

-continued

```
                515                 520                 525
Gly Val Trp Gln Pro Ala Ala Gln Pro Lys Arg Arg His Arg Gln
        530                 535                 540

Asp Ala Leu Pro Gly Pro Cys Ile Ala Ser Thr Pro Lys Lys His Arg
545                 550                 555                 560

Gly

<210> SEQ ID NO 2
<211> LENGTH: 20
<212> TYPE: PRT
<213> ORGANISM: Artificial
<220> FEATURE:
<223> OTHER INFORMATION: Synthetic

<400> SEQUENCE: 2

Thr Ser Asp Ala Cys Met Met Thr Met Tyr Gly Gly Ile Ser Leu Leu
1               5                   10                  15

Ser Glu Phe Cys
            20
```